(12) United States Patent
Belassel et al.

(10) Patent No.: US 8,477,905 B2
(45) Date of Patent: Jul. 2, 2013

(54) NON-DESTRUCTIVE TESTING SYSTEMS AND METHODS

(75) Inventors: Mohammed Belassel, Windsor (CA); E. Michael Brauss, Amherstburg (CA); James A. Pineault, Windsor (CA); Robert John Drake, Windsor (CA)

(73) Assignee: Proto Manufacturing Ltd., Ontario (CA)

( * ) Notice: Subject to any disclaimer, the term of this patent is extended or adjusted under 35 U.S.C. 154(b) by 362 days.

(21) Appl. No.: 12/727,999

(22) Filed: Mar. 19, 2010

(65) Prior Publication Data
US 2010/0239068 A1    Sep. 23, 2010

Related U.S. Application Data

(60) Provisional application No. 61/162,098, filed on Mar. 20, 2009.

(51) Int. Cl.
*G01N 23/20*    (2006.01)

(52) U.S. Cl.
USPC ............................................................ 378/72

(58) Field of Classification Search
USPC ....... 378/72, 73, 79, 81, 70; 250/306; 73/602; 324/238
See application file for complete search history.

(56) References Cited

U.S. PATENT DOCUMENTS

| | | | |
|---|---|---|---|
| 2,738,671 A | 3/1956 | Fiske, Jr. et al. |
| 4,902,583 A | 2/1990 | Brucker et al. |
| 4,972,448 A | 11/1990 | Munekawa |
| 6,072,568 A | 6/2000 | Paton et al. |
| 2003/0192385 A1 | 10/2003 | Uhlik et al. |

OTHER PUBLICATIONS

PCT International Search Report and Written Opinion of the International Searching Authority for International Application PCT/US2010/028007 dated May 18, 2010, 8 pages.

*Primary Examiner* — Jurie Yun
(74) *Attorney, Agent, or Firm* — Fitch, Even, Tabin & Flannery, LLP

(57) ABSTRACT

A system and method for non-destructively determining the grain orientation of a crystalline material using x-ray diffraction techniques to non-destructively analyze material and, more particularly, to a system and method for determining the grain orientation of an underlying crystalline material covered by an overlying polycrystalline material. Further, the system and method relate to the use of x-ray diffraction to non-destructively characterize parts and components to determine whether to accept or reject those components or parts for use in application.

32 Claims, 10 Drawing Sheets

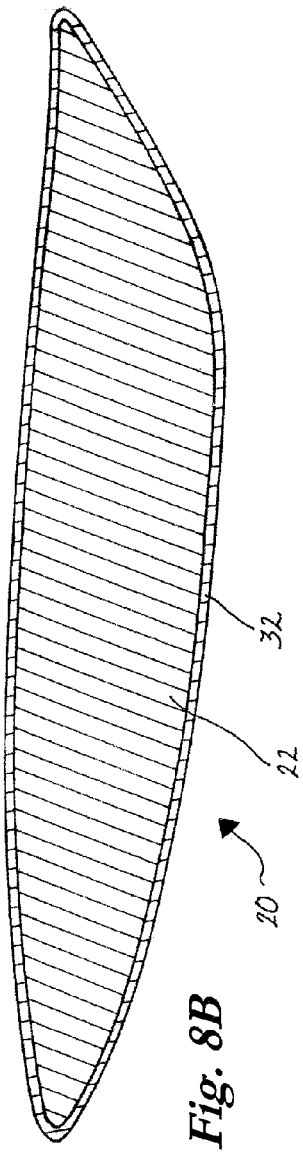
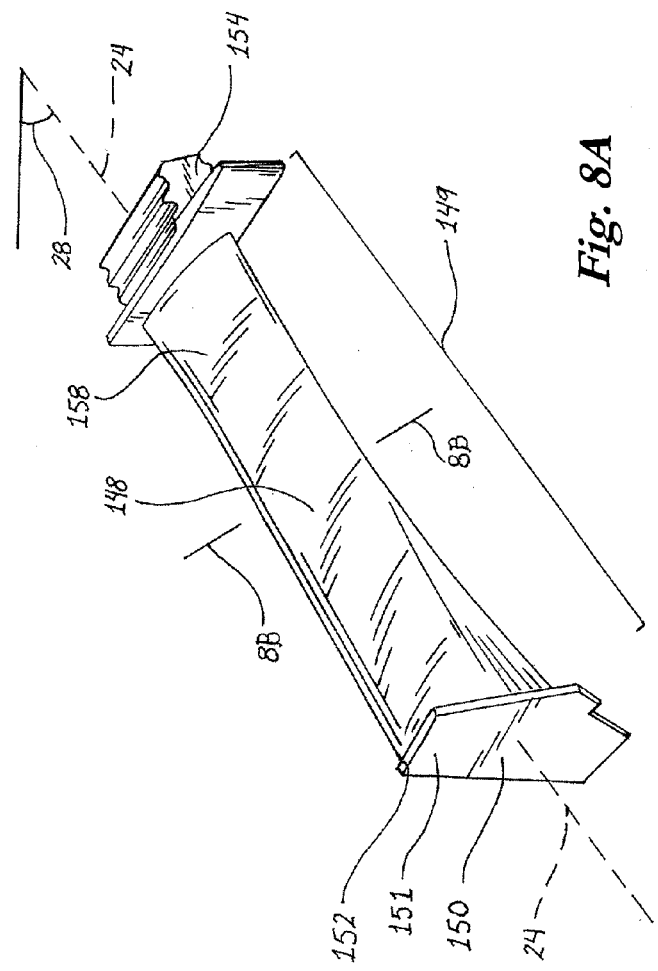
Fig. 8B
Fig. 8A

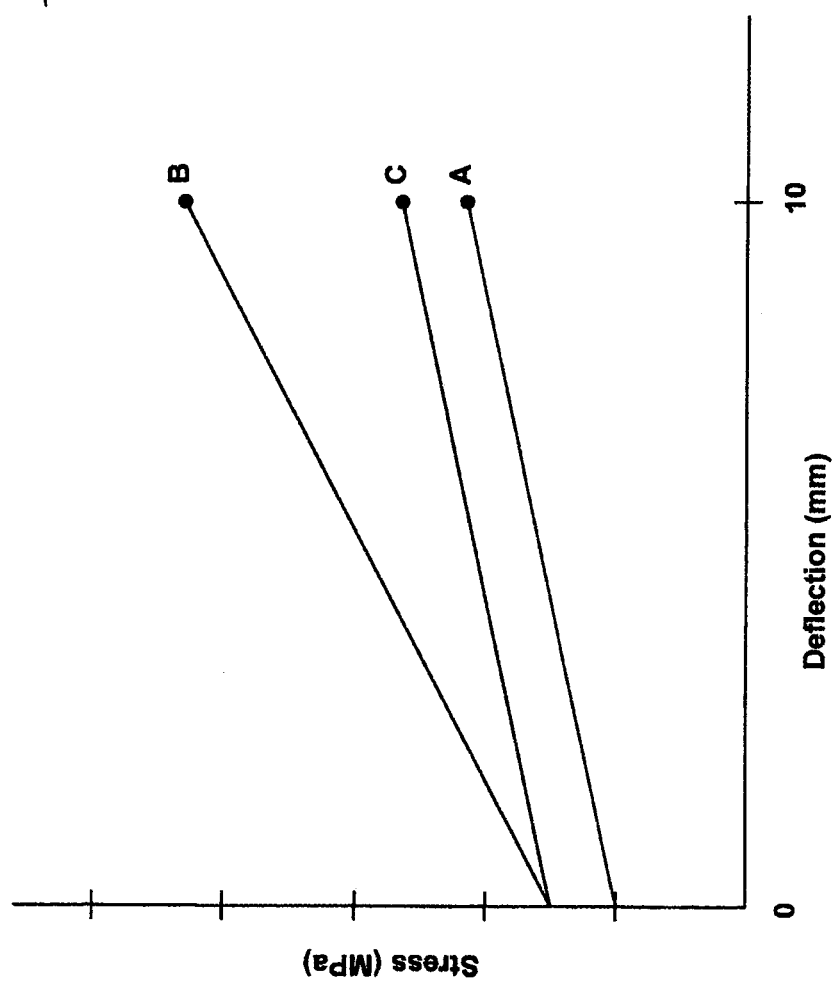

NON-DESTRUCTIVE TESTING SYSTEMS AND METHODS

CROSS-REFERENCE TO RELATED APPLICATION

This application claims benefit of U.S. Provisional Application No. 61/162,098, filed Mar. 20, 2009, which is hereby incorporated herein by reference in its entirety.

FIELD OF THE INVENTION

The invention relates to a system and method for non-destructively determining the grain orientation of a crystalline material using x-ray diffraction techniques to non-destructively analyze material and, more particularly, to a system and method for determining the grain orientation of an underlying crystalline material covered by an overlying polycrystalline material. Further, the field relates to the use of x-ray diffraction to non-destructively characterize parts and components to determine whether to accept or reject those components or parts for use in application.

BACKGROUND OF THE INVENTION

Fatigue-limited metal components of gas turbines or jet engines, or other machine components subject to metal fatigue or failure, are carefully managed in order to avoid failure during operation. The failure, for example, of a critical component of a jet engine during operation may result in the loss of life or other catastrophic consequences. Therefore, the industry researches, designs, and produces components to provide greater strength and durability to avoid such situations.

Single crystal (SX) materials and directionally solidified (DS) materials have considerable advantages over materials cast using conventional methods. For example, in conventionally cast materials, there are large numbers of grain boundaries. These grain boundaries often present weakness points in the plane normal to the loading direction along which premature damage can occur. In addition, the low modulus of the grain in the loading direction helps reduce the stress applied to the material. These grain boundaries in the plane normal to the loading direction are essentially eliminated in SX and DS materials. Rather, the SX and DS materials have a more uniform structure and grain orientation. This uniform structure imparts enhanced directional strength characteristics and enhanced thermal fatigue resistance. These characteristics make DS and SX materials ideal for use in applications where strength and heat resistance are paramount. For example, SX and DS materials are used in the formation of turbine blades.

In addition to their favorable strength and heat resistance properties, materials incorporating metals or other substances which have directionally solidified grains (DS) or are composed of a single crystal (SX) are used in applications where the combination of exceptional strength and light weight are important. These materials are known as anisotropic materials, meaning they have directionally associated properties. When designing components or parts that are to be composed of DS or SX materials, the orientation of the grain of the crystal is aligned to provide the highest amount of strength to provide exceptionally strong and fatigue resistant materials without having to increase their weight to achieve these properties. Ideally, these DS and SX materials have an extended service life and are less prone to catastrophic failure. For example, DS and SX material are ideal for use in applications such as turbine blades in jet engines. However, if during production, the grain of the crystal is incorrectly oriented with respect to the direction of high stress loading the part experiences in service, the optimum strength characteristics may not be realized.

Single crystal materials are formed of a crystalline solid wherein the crystalline lattice of the material is continuous and unbroken to the edges of the material. Therefore, in SX material, there would not be grain boundaries within the material. Directionally solidified grain materials have a similar crystalline composition to single crystal materials, with the exception that there may be one or more grains, and therefore sets of grain boundaries parallel to the loading direction, within the material.

Forming SX and DS materials presents a number of production problems. An assortment of variables can affect the microstructure of solids. For example, the presence of impurities can affect the formation of the of the SX or DS material. Further, crystallographic defects and dislocations can occur during formation. For these reasons, single crystals of a significant size are rare in nature and are difficult to engineer even under strictly controlled conditions laboratory or industrial conditions. Grain boundaries can have an effect of the physical properties of materials relative to single crystal materials, but materials having directionally solidified grains can still offer significant strength improvements over materials not having directionally solidified grains.

Both SX and DS material have a crystalline structure which has a specific directional orientation that provides the optimum strength characteristics. It is this specific crystalline orientation that imparts the exceptional strength characteristic to these materials. Hence, it is in the interest of a manufacturer to control the formation of the SX or DS material to eliminate impurities and to control, or at least be aware of, the directionality of the crystalline or grain orientation in the material. Decisions to accept or reject the component are based on the orientation of the SX or DS crystal or grains.

During the formation of SX and DS materials, it is particularly important to avoid the occurrence of mal oriented grains (MOGs). The presence of MOGs in SX and DS material can have a significant impact on the directionally enhanced strength characteristics of the material. Once a SX or DS material has been formed, any imperfections or MOGs are an inherent part of the material and have an impact upon the strength characteristics of the material. Undetected MOGs can be a contributing factor in reducing the useful life of components or parts composed of SX and DX materials such as turbine blades. Additionally, it is vital that the grain orientation of the material correctly coincide with the appropriate direction of the desired enhanced strength of the part in order to ensure the desired properties of the SX and DS material in the blade.

Determining the grain orientation of an SX or DX material where the single crystal itself is exposed can be simply determined using standard LAUE and/or pole figure techniques employing x-ray diffraction. In this instance the x-ray beam is directed at an exposed surface of a crystal and a diffracted crystal lattice pattern is detected by interposing a detector on the diffracted beam path such that the LAUE and pole figure techniques can be employed. If access to the SX or DS crystal is not available for non-destructive testing thereof, for example such as if a surface of the SX or DS material is not exposed to the x-rays, the LAUE and pole figure techniques could not be used because the proper x-ray diffraction from the SX or DX material would be unable to be captured to determine the orientation of the material due to the interference of the x-rays by material masking the SX or DS material.

X-ray emitters and x-ray detectors and their use in x-ray diffraction techniques for measuring residual stresses in crystalline substances such as metal or ceramic materials are known. In these techniques, x-ray diffraction is utilized to subject the outer surface of the material to x-ray radiation with the resulting observed x-ray diffraction peak interpreted to arrive at a measurement of a strength related characteristic, i.e., stress, retained austenite, hardness of the part material, to show, for instance, the level of fatigue damage present in the material.

The current practices for the measurement of grain orientation in SX and DS materials where the SX or DS crystal obfuscated involve mechanical sectioning of the material to form a coupon which is then analyzed. Once the coupon is obtained, the crystalline structure of the material can then be analyzed using x-ray diffraction or visual metallographic inspection. However, since this process does require mechanical sectioning to perform the analysis, the actual material that will be present in, for example a turbine blade, is not directly tested. Rather, it is just a representative portion of the total material that was used to separately form the blade. Therefore, this method of fabricating a coupon for determining the crystalline structure would be considered a destructive method as the blade itself is destroyed and would be impossible to subsequently place the blade into service. Another method is to expose the underlying crystal by removing material preventing direct characterization of the SX or DS material via x-ray diffraction. However, removal of material to expose the underlying crystal could affect the strength characteristics of the component and for the purposes of this disclosure would also be considered a destructive method.

SUMMARY OF THE INVENTION

In certain articles, it has been determined that during manufacturing the host material can be reorganized to develop an outer layer of skin thereon of material that substantially prevents the original host material from being non-destructively tested for certain material strength characteristics. Particularly, it has been determined that during post-production treatment of components made of SX and DS materials, an overlying polycrystalline layer often forms over the exterior of the component. The polycrystalline layer may form, for example, during heat treatment, blast peening, or during the final shaping of the product. The presence of such an overlying polycrystalline layer can prevent direct analysis of the underlying crystal orientation using the LAUE and or pole figure techniques. While, for example, the orientation angle of the underlying material may not be able to be directly tested due to the presence of the overlying polycrystalline layer, it has been discovered that the overlying layer is directly responsive to variations in the underlying material under different loading conditions. More specifically, while it may not be possible to directly measure the crystal orientation of the underlying SX or DS material due to the presence of the overlying polycrystalline layer, it has been determined that the overlying layer is directly responsive to variations in the crystal orientation present in the underlying SX or DS layer of material under certain loading conditions.

Accordingly, in one aspect, methods of measuring a material characteristic of one material in an article having different materials to determine a material characteristic of a different material of the article are provided. As discussed above, certain materials of an article may not be available for direct analysis by conventional methods without destructively modifying the article. By measuring a material characteristic of the one material under different testing conditions, such as by applying differential loading conditions to the article, the material characteristic can then be compared to similarly tested articles having known characteristics of the different material to determine the unknown characteristic of the tested article.

In another aspect, a method is provided for determining a certain material characteristic of an article to be tested where the article is of different materials with one of the materials being responsive to the other when subjected to predetermined test conditions. The method includes measuring material characteristics of a predetermined material under different predetermined test conditions on articles similarly configured to the article to be tested and correlating these measurements to material characteristics of a different material of the similarly configured articles. The correlated data may then be used in comparison to information gathered during measuring the material characteristic of the predetermined material under the different predetermined testing conditions for the article to be tested to determine the material characteristic of the different material in the article without requiring direct measurement of the characteristic of the different material. By utilizing the method of the invention, the tested articles may then be placed into use in an application because they have not undergone destructive testing.

More particularly, applicants have discovered that in articles that have an underlying crystalline material and an overlying polycrystalline layer, the residual stress characteristics of the overlying polycrystalline layer, when measured under different loading conditions, are responsive to the elastic properties of the underlying crystalline material experiencing and responding to these different load conditions. As previously discussed, the orientation of the grain of a crystalline material in an article directly affects the strength properties of the article. If the grain of the crystal is, for example, aligned with the longitudinal axis of the article, the crystalline material article will display certain elastic properties when a load is applied to a specific location on the article to generate a predetermined amount of deflection of the article. However, if the grain of crystal is not aligned with the longitudinal axis of the article, the article will display different elastic properties when the same load is applied to the same location on the article. As the angle of the underlying crystalline material varies in relation to the article's longitudinal axis, so does the elastic properties of the article when exposed to loads.

As mentioned, variations in the elasticity of the underlying material can have an effect on the material in the overlying polycrystalline layer, and specifically the residual stress of the polycrystalline layer. By analyzing the overlying layer of a tested article having unknown material characteristics in the underlying material, one is able to compare the analysis of the overlying layer to similarly analyzed articles having known material characteristics of the underlying material to determine the unknown material characteristic of the tested article.

As discussed above, by recognizing the overlying material of an article to be tested is responsive to underlying material when the article is subjected to differential loading conditions, it has been determined that x-ray diffraction techniques can be utilized to analyze the overlying material where the underlying material cannot be properly tested with x-ray diffraction techniques, to determine material characteristics of the underlying material. In order to determine grain orientation of a crystalline material having an overlying layer of polycrystalline skin, previously this determination would require destructive removal of at least some of the polycrystalline skin to allow the x-rays to access the underlying crystalline material. While this provides an accurate determination of the grain orientation of the crystalline material, the destructive removal of the polycrystalline skin alters the geometry and strength characteristics of the article and can render it undesirable for use. Therefore, when analyzing a group of articles, a representative sample of the articles would be selected and destructively tested. While this destructive testing would provide, for example, an orientation angle of the crystalline material of the article, the tested samples could no longer be used in an application. Based on those samples tested, decisions would be made regarding the remaining articles of the group. By contrast, the system and method herein allow each article of a group to be analyzed in manner that is non-destructive so that each article may then be used in an application if the material characteristics for that article are found to be acceptable.

Herein, it has been determined that by measuring the stress of the polycrystalline layer under different loading conditions and calculating a slope between points defined by the measured residual or total stresses and the corresponding applied loads at which the stresses are measured, the generated slope could be compared to previously calculated slopes for similarly configured articles correlated to known underlying crystal orientation angles to determine the crystalline orientation angle of the tested article. Accordingly, for the purposes of the present disclosure, the term "stress" as used in the context of measuring a stress value in the overlying layer of an article will be understood to mean "residual stress" when the article is measured in without a load applied and to mean "total stress" when the article is measured with a load applied. "Applied stress" is generated when the article is placed in a loaded stated. Hence, the term "total stress" will be understood to be the cumulative amount of "residual stress" plus "applied stress".

Further, it is desirable to be able to test the articles themselves that are subject to being placed into service, rather than testing representative samples of a group of these articles and placing untested articles from the group into service based on the results for the representative samples. If an article is determined to have a material characteristic of the underlying material that could possibly result in early failure of the part, that particular part may be selected to be retired and not placed into service, rather than retiring all of the articles from a group with the tested article being just a representative sample from that group.

Accordingly, an x-ray diffraction system and method are provided for non-destructively testing an article having a material that is currently tested by destructive testing methods. Such a system and method allow an article to be tested and then that same article to be placed into service after it has been characterized as no destructive testing methods have been used. In one form, an x-ray diffraction apparatus is provided that applies differential loading on the article to alter and analyze a characteristic of an overlying material layer that is responsive to one or more properties of an underlying material. The analysis of the overlying layer of material under the different loading conditions may then be used to indirectly determine a characteristic of an underlying material.

More specifically, in the above system and method, the article is preferably tested in an unloaded condition thereof so that there is no deflection of the article. Thereafter, a sufficient load is applied to the article to generate a predetermined deflection thereof. Accordingly, the term "differential loading" encompasses zero load on the article and the load necessary to achieve the desired deflection of the article. Further, when discussing "loads" or "loading" herein it will be understood that the measurements and calculations based on the applied loading can use corresponding values of deflection distance instead.

In one preferred x-ray diffraction apparatus, a mounting device and a load applying mechanism are provided, with the load applying mechanism capable of exerting a predetermined load on an article to generate a predetermined deflection distance of the article. The mounting device is configured to hold the article to be tested. In one form, the mounting device fixedly retains one end of the article, and the load applying mechanism is configured to deflect the opposite end of the article by a predetermined distance. For this purpose, preferably the mounting device is configured to hold an elongate article to extend in a cantilevered fashion therefrom so that the load applying mechanism applies a load to the free end of the elongate article. In this manner, when the predetermined load is applied to the article, the article will bend and deflect. In this regard, the predetermined load applied to the article should be such that the article is able to elastically, reversibly and resiliently return to its original, non-deflected condition and the article's strength characteristics have not been adversely affected. For example, after the load has been removed, the strength and/or other material characteristics of the article should remain substantially unchanged relative to the article prior to the application of the predetermined load thereto. If excessive loading is applied to the article so as to adversely affect a strength-related material characteristic thereof such a change would be considered destructive to the article.

The preferred x-ray diffraction apparatus includes a known x-ray emitter and x-ray detector. Any arrangement of the x-ray emitter and x-ray detector is acceptable as long as the emitter can direct x-rays at the article and the detector is positioned to detect x-rays diffracted from the article as it is tested under different loading conditions. For example, various parts and arrangements of the emitter and detector may be required based on various part sizes and configurations and may be arranged such that the desired x-ray diffraction technique may be performed. Examples of such arrangement may be found in, for example, applicants' assignee's U.S. Pat. Nos. 6,925,146 and 7,283,612, which are incorporated herein by reference.

In another aspect, an x-ray diffraction system capable of generating differential loading, or deflection, on an article to be tested is provided including a controller connected to an x-ray diffraction device and a load applying device for non-destructively determining a material characteristic of an underlying material of an article under an overlying material. As discussed above, it is advantageous to be able to measure a material characteristic of an underlying material on an article to be tested without damaging the article to be tested. By generating different load conditions on the article that do not affect the final condition of the article after testing, and measuring a material characteristic of the overlying material under the different load conditions, the present x-ray diffraction system non-destructively determines the material characteristic of the underlying material.

In one form, the controller for the x-ray diffraction system includes a processing unit that is configured to calculate a slope value between points defined by measured material characteristics of the overlying material and the corresponding different loading conditions at which the material characteristic is measured. The controller has a memory unit that stores a database of information relating to similarly configured articles with the information being known slopes between points defined by measured material characteristics of overlying material and loading conditions at which the material characteristics are measured with the slopes correlated to known material characteristics of underlying material. This information in the database stored in the memory unit may then be referenced by a comparison unit of the controller to determine the material characteristic of the underlying material in the tested article.

Herein, it should be understood that while the controller could be comprised of a single housing in which the processing, memory and comparison units and electronics therefore are contained, these units can be physically separated from each other and even provided at remote locations from the x-ray diffraction testing apparatus accessible via wireless links. In addition, the units themselves can have component parts that are separated from each other so that, for example, not all of the parts of the processing unit need be contained in the same housing. As is known, with such a controller or control system the physical location of the functional units thereof is not critical to their operability but rather what is relevant is that they have the desired functionality and electrical intercommunication described herein. Further, the controller may be configured so that when operation of the x-ray diffraction apparatus is initiated, any or all of the aspects and steps of the x-ray diffraction testing procedure described herein to conduct the analysis of an article for non-destructively determining the characteristics of its underlying material are undertaken automatically.

Again, one of the advantages of the x-ray diffraction system is the ability to test articles to determine a material characteristic of an underlying material in an article, and then being able to place that article into service. The system allows for rapid testing of all articles that are going to be placed into service by providing a non-destructive testing system that can quickly and accurately determine if a desired characteristic is present that is otherwise typically not able to be determined without performing a destructive analysis on the article. This type of testing is of particular importance with parts like rotor blades that can be placed in service, for example, in a jet engine. While destructively testing a representative sample of blades from a manufactured lot may provide certain statistical assurances as to the nature of the remaining blades that are to be placed in service, by testing the actual blades that are being placed in service, further assurance that the actual blades in service contain the desirable material characteristics may be provided.

For the purposes of the present disclosure, the term "destructive testing" includes testing that requires removal of all or some of an overlying material layer to gain access to an underlying material for testing thereof. For example, this may include the removal or thinning of a polycrystalline layer in order to provide access to an underlying crystalline material for direct testing such as by x-ray diffraction testing. Destructive testing would also be considered to include mechanical sectioning, for example, by cutting into or through the article to access the underlying crystalline material to get a coupon thereof for testing purposes. Furthermore, destructive testing would further include applying a load to the article of a magnitude that would damage, permanently deform, or otherwise, negatively affect a strength, residual stress, or elastic characteristic of the article.

In another aspect, a method for determining an unknown orientation angle of a crystalline material in an article having an overlying polycrystalline layer is provided. As described above, the method allows for non-destructively testing the article such that the article may be placed into service after determination of the orientation angle. Thus, the method allows for testing of all articles that are to be placed into service as compared to a destructive test which would only test a representative sample of articles, which after testing would not be able to be placed into service.

In one aspect of the method, stress is measured in the polycrystalline layer of the tested article under different loading conditions. The measured stress can be plotted against the load at which it was measured, and a slope is calculated between the points of the measured stress values and the corresponding load values at which the stress values were measured. The slope is then compared to previously determined slopes of similarly configured articles having known orientation angles of the underlying crystalline material to determine the crystal orientation angle in the tested article. Based on the determination of the orientation angle of the underlying crystalline material, a decision may be made regarding whether the tested article is placed into service.

BRIEF DESCRIPTION OF THE DRAWINGS

FIG. 8A is a perspective view of a rotor blade;

FIG. 8B is a cross-sectional view of the rotor blade of FIG. 8A taken along line 8B-8B showing an outer polycrystalline layer in overlying relation to underlying crystalline material;

FIG. 9 is a representative graph plotting stress measurements at zero load and with the blade loaded with a predetermined load for three blades and showing the slopes of stress versus load for each blade;

DETAILED DESCRIPTION OF THE PREFERRED EMBODIMENTS

Figure 1:
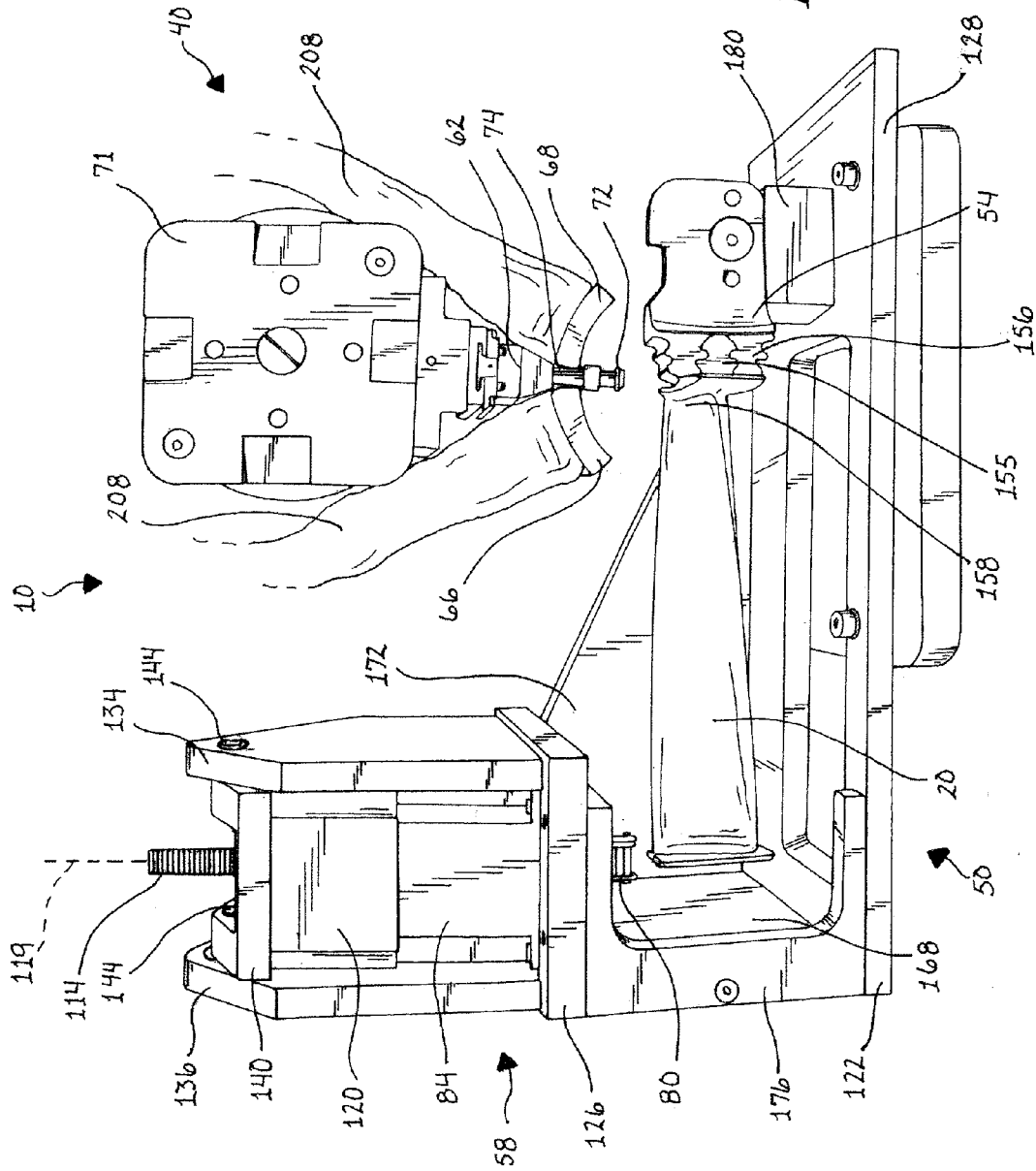
FIGS. 1-3 are a perspective views of an x-ray diffraction system in accordance with the present invention showing an x-ray diffraction testing apparatus including an x-ray diffraction device, and a load applying device including a fixture for holding a rotor blade.

Referring FIGS. 1-4, an x-ray diffraction system 5 including an x-ray diffraction apparatus 10 for analyzing a representative article 20 in accordance with the present invention is illustrated. The article 20, as depicted in FIG. 8A, may, for example, be a rotor blade for use in a turbine. The blade 20, as shown in cross-section in FIG. 8B, is depicted as having two materials. The main body 22 of the blade 20 is a crystalline material, such as a SX material or DS material as previously described. These materials are widely used when low weight and certain material characteristics, such as high strength characteristics, are important. The crystalline material 22 has a further material characteristic, namely grain orientation, which when properly aligned with the highest stress direction of the article 20 provides an article with a greater amount of stress resistance than if the grain orientation was out of alignment with the proper alignment. Further, as strength, elastic, and stress properties of crystalline material 22 are grain orientation specific, the grain orientation in the blade 20 affects how the material characteristics of the crystalline material 22 react when the blade 20 is placed under a load. For example, the proper grain orientation to provide the highest stress resistance may be a grain orientation that is aligned with the longitudinal axis 24 of the blade. If during manufacture of the blade 20, the orientation angle of the grain is misaligned from the blade axis 24 to be at an angle 28 that deviates from the preferred orientation then the strength characteristics of the underlying material may be lower relative to a blade having a proper grain orientation. Incorrect orientation of the grain may result in an increased failure rate for such a blade. Similarly, the elasticity of the crystalline material 22 in the blade 20 if aligned with the axis 24 will have a certain elasticity value, but if the grain orientation is misaligned with the axis, the crystalline material will exhibit a different elasticity value.

As discussed above, the grain orientation of SX and DS materials may be determined if an exterior surface of the crystalline material 22 is available as by being exposed to be analyzed by techniques well known in the art, for example, by LAUE, pole figure, metallurgical, electron microscopy, sonic analysis, ultrasonic analysis, eddy current techniques, electromechanical techniques, electromagnetic techniques, metallurgical techniques, and other techniques.

It has been determined that at some point during or after the manufacturing process, for example, during the final shaping, heat treatment, or peening of the exterior surface of the blade 20, the outermost portion of the crystalline material 22, loses its single crystal organization and reforms as an overlying polycrystalline layer 32. The polycrystalline layer 32, rather than having a single grain orientation, has a plurality of grain orientations. The polycrystalline layer may be of varying thickness dependent on the processes that the blade 20 undergoes during manufacture. For example, the polycrystalline layer 32 may be in a range from a one molecule thickness to 100 microns or more. The presence of the polycrystalline layer 32 over the crystalline material 22, in general, prevents direct analysis of the crystalline material by the techniques for direct analysis of a crystalline material as discussed above. For the purposes of this invention, the presence of a polycrystalline layer 32 at any thickness is sufficient to practice the invention, although the thickness of layer 32 in FIG. 8B is greatly exaggerated for illustration purposes with respect to the thickness typical with a polycrystalline overlying material layer as described herein The generally disordered nature of the polycrystalline layer 32 in effect masks, or shields, the crystalline material 22 from x-ray diffraction and other material characteristic testing techniques. In theory, if the polycrystalline layer 32 was thin enough and a high power x-ray was used, it may be possible to pass x-rays through the polycrystalline layer 32 to the underlying crystalline material 22. However, in general, in order to access the crystalline material 22 at least a portion of the polycrystalline layer 32 must be removed to provide access to the crystalline material 22 for direct testing of the crystalline material to determine the grain orientation. Nonetheless, as previously discussed, the removal of any portion of the polycrystalline layer 32 can affect, for example, the strength, stress, and elastic properties of the blade 20 and would be considered "destructive" techniques for the purpose of this application. The removal of a portion of the polycrystalline layer 32 may include, for example, removing a small area of the polycrystalline layer 32 to provide a "window" to the underlying crystalline material 22. The removal may also include removing up to all of the polycrystalline layer 32 or sectioning the blade to provide a cross-section, or coupon, of the blade, thereby exposing the underlying crystalline material 22.

Figure 2:
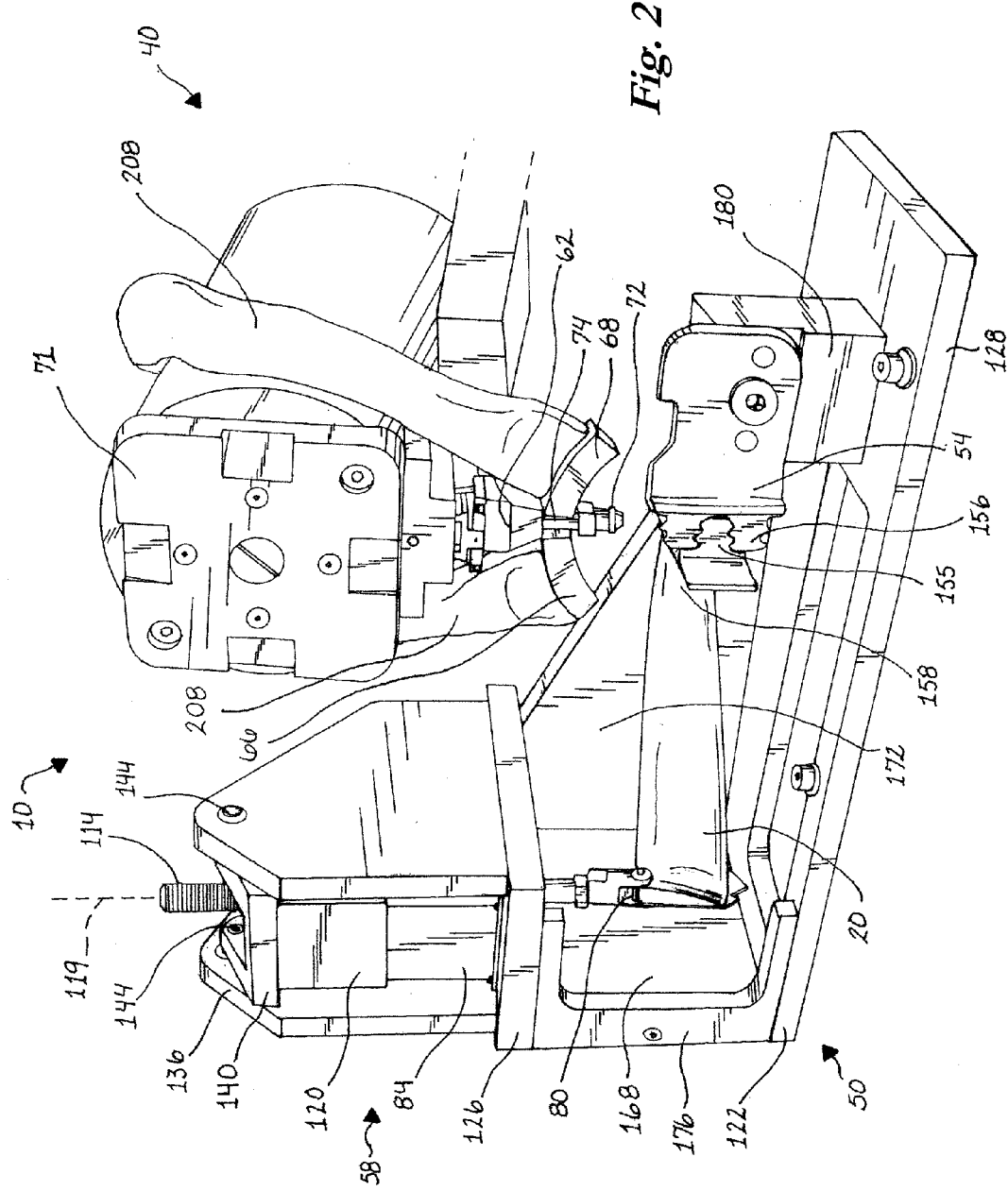
Figure 3:
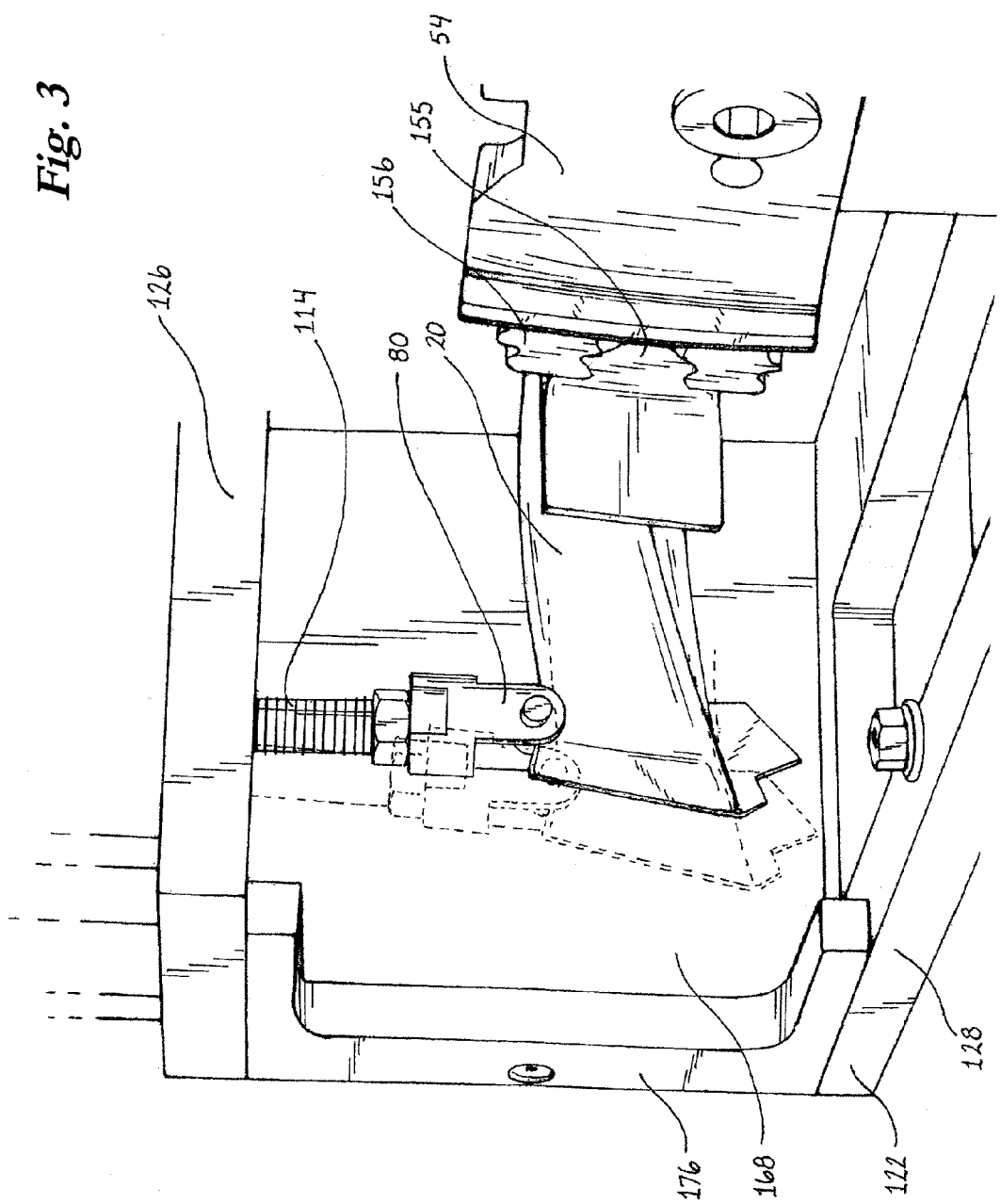
Figure 4:
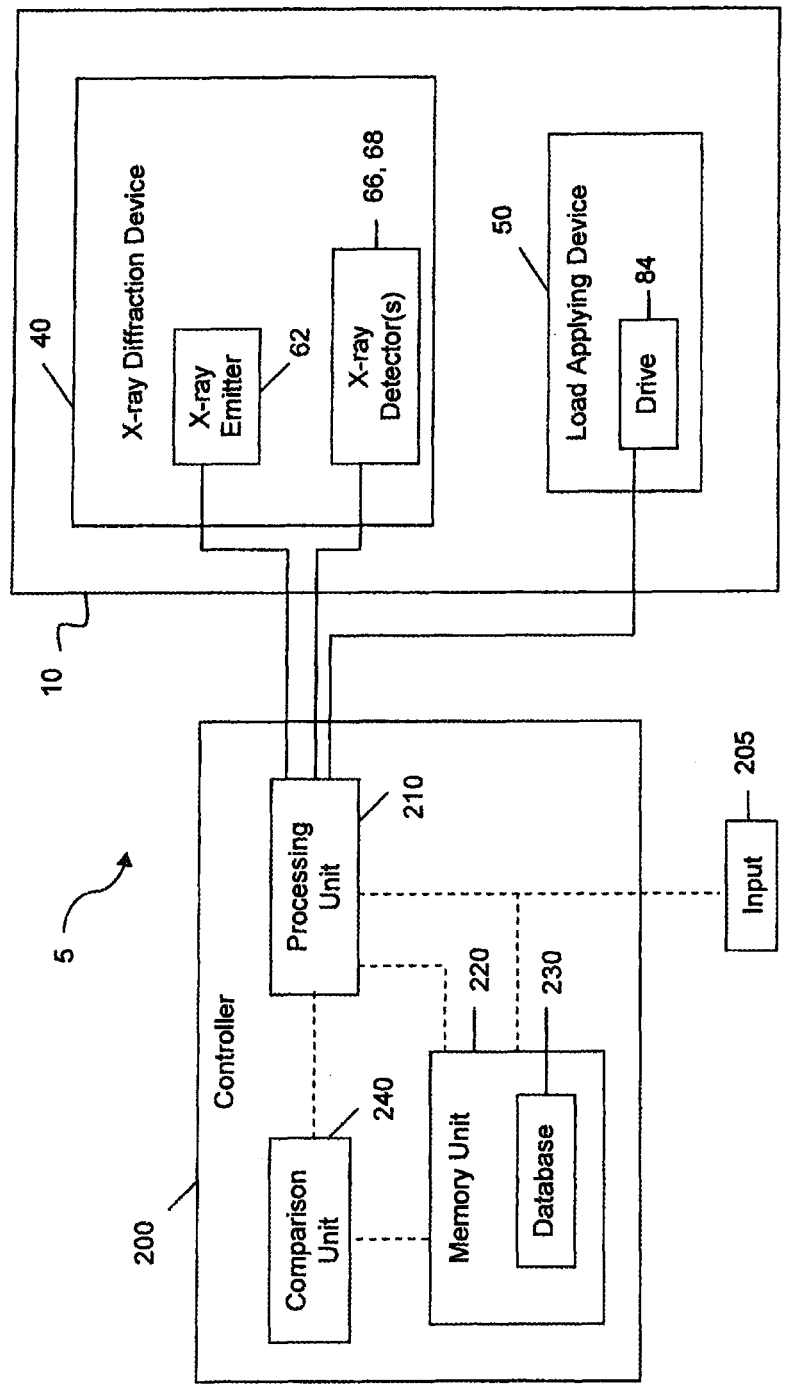
FIG. 4 is a schematic view of a control system for the x-ray diffraction testing apparatus.
Figure 5A:
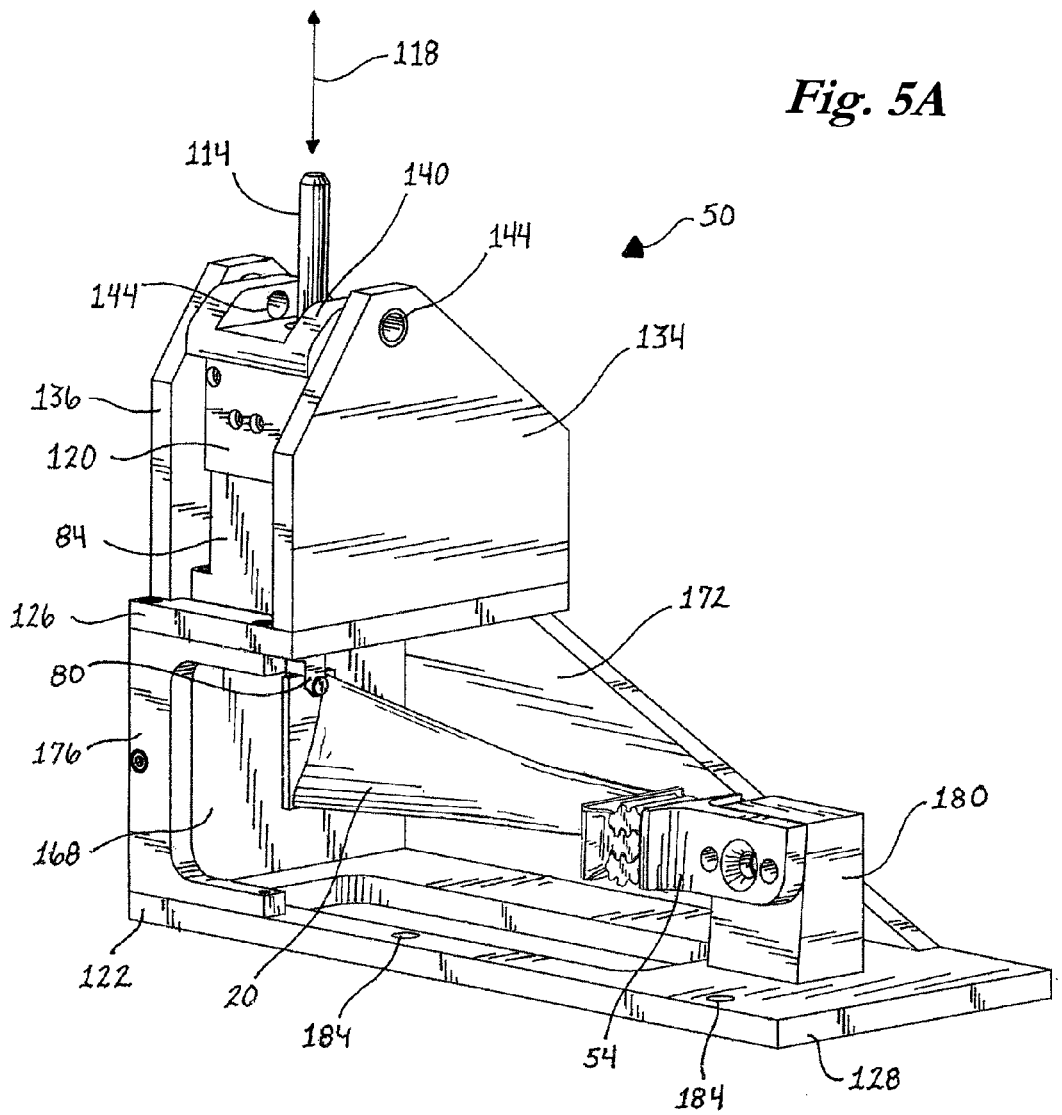
FIG. 5A is a perspective view of the load applying device and the fixture holding the rotor blade at one end to extend under the load applying device at the other end of the blade.
Figure 5B:
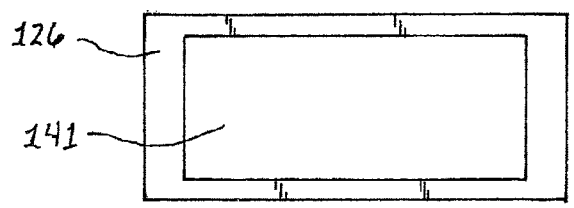
FIG. 5B is a perspective view of the horizontal support member of the load applying device of FIG. 5A with an opening therethrough to allow pivoting of the drive assembly.

Referring to FIGS. 1-3, an x-ray diffraction apparatus 10 for use in the x-ray diffraction system 5 herein is illustrated including an x-ray diffraction device 40 and a load applying device 50. The load applying device 50 can be provided with a mounting device 54 configured to hold the article 20 to be tested and a load applying mechanism 58 for exerting a predetermined load on the article. As will be further discussed, the load applying mechanism 58 is operable to generate differential loading conditions on the article, and specifically the rotor blade 20.

The x-ray device 40 has an x-ray emitter 62 and at least one, and preferably two, x-ray detectors 66 and 68. The x-ray emitter 62 can include an elongate x-ray head 71 having a collimator 72 depending from one end thereof and which bisects an arc-shaped detector mount 74 having the detectors 66, 68 fixed toward either end thereof as typically employed in x-ray diffraction units that measure residual stress for metal, ceramic, or crystal materials. The emitter 62 may be selected for the specific wavelength generated to tailor the x-rays generated to the article 20 being tested so as to better match the structure being analyzed. This may be accomplished by varying the material for the anode of the emitter. Exemplary anode materials include copper, cobalt, wolfram, silver, molybdenum, manganese, iron and titanium. The beam shape can be further adjusted by providing different collimators 72 on the x-ray emitter 62.

In addition to the emitter 62, the x-ray device is further provided with one or more x-ray detectors or sensors 66 and 68 which are typically mounted on either side of the collimator 72. The detectors 66 are typically mounted in an arcuate manner on an arc-shaped mount 74 so as to be positioned on either side of the collimator 72, as depicted, although the arrangement of the detectors 66, 68 may vary relative to each other and in relation to the collimator 72 dependant upon the measurement technique being used and to match the wavelength being generated by the emitter 62. Further, the x-ray device 40 may be provided such that it may be shifted in a plurality of liner directions such as in the vertical Z-axis direction as well as in the lateral Y-axis direction. X-axis fore and aft direction shifting of the x-ray device 40 can also be provided as well as rotary or pivot shifting about different pivot axes. For example, to determine the stress of an article 20 using the d v. $\sin^2 \Psi$ technique, at least two measurements at different $\Psi$ angles must be measured. Therefore, if a single emitter 62 is to be used, the x-ray device should be shiftable to provide at least two $\Psi$ angle measurements. Additionally, single exposure, double exposure, or similar techniques may used to determine residual stress. Further, the x-ray diffraction device may be used to detect strain in the polycrystalline layer. As is known in the art of x-ray diffraction, strain is calculated as the change in the spacing distance (d) between atomic planes and is generally calculated as $\Delta d/d$. As discussed above, examples of such arrangement may be found in applicants' assignee's U.S. Pat. Nos. 6,925,146 and 7,283,612, which are incorporated herein by reference.

The load applying device 50, as shown in FIGS. 1-3, 5 and 6, includes a bearing member 80 for contacting and engaging the article 20 when applying a load to the article 20 and a drive 84 for driving the bearing member 80 into engagement with the article 20. The bearing member 80 may be of any form that is capable of engaging and maintaining contact with the article 20 during the application of the load to the article. It should be noted that it is desirable for the bearing member 80 to avoid damaging the surface of the article 20 while engaged with and applying a load to the article. For example, a bearing member should be able to apply a deflecting force to the material without generating large frictional forces thereagainst that could damage the article such as by scraping or otherwise marring the surface of the article 20.

Figure 7:
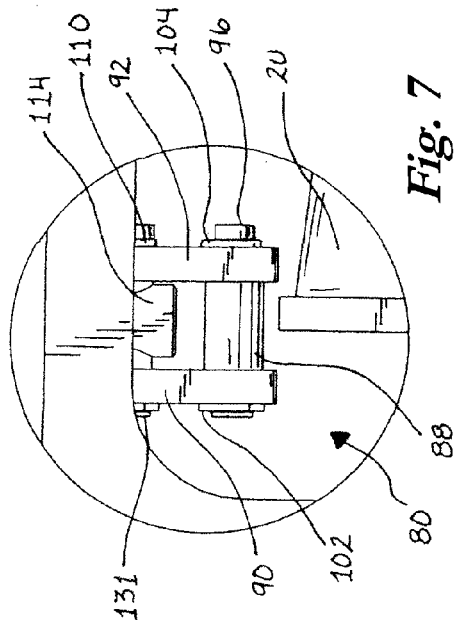
FIG. 7 is an enlarged view of the rolling bearing member of FIG. 6 showing a bracket assembly for the roller bearing member which extends between a pair of bracket legs pivotally connected to the drive screw.

In the illustrated and preferred form, the bearing member is a rolling bearing member 80. Referring to FIG. 7, the rolling bearing member or assembly includes a rolling shaft or sleeve member 88 that is supported by opposing bracket legs 90 and 92 having openings passing therethrough appropriately sized to accommodate the axle member 96 of the roller shaft or sleeve member 88 extending therethrough. For example, the axle member 96 may be provided with an enlarged flange portion 102 at one end of the axle member 96 sized larger than the hole in the bracket leg 90. The other end may be prevented from slipping back through the hole in the bracket leg 92 by providing, for example, an engaging member 104 that engages a groove 106 in the axle member 96 positioned to prevent the axle member 96 from sliding back through the bracket leg 92. The rolling bearing member 80 is provided to roll along a contact surface of the article 20 and thereby reduce friction with the article 20 while applying a load thereto.

The drive 84 of the load applying mechanism 58 may be any type of motor capable of driving the bearing member 80 in a predetermined direction to engage the article 20. The drive 84 should be capable of providing a predetermined load to generate a predetermined deflection distance or strain amount on the article 20 by driving the bearing member 80 into engagement with the article 20 and maintaining that predetermined load during a period of time sufficient to take a measurement using x-ray analysis on the article 20. The load applying mechanism 58 may also include a driven member 114 that is shifted in a predetermined direction 118 along the driven member axis 119 toward the article for applying the predetermined load to the article 20. The driven member may be in the form of a translation screw 114 that is driven in a generally vertical direction 118 by the drive 84 of the drive assembly 120 for applying the load to the article 20. In this regard, the motor 84 may house a drive nut that is rotated to cause the translation screw to linearly advance or retract along the screw axis 119. However, the driven member 114 may be of any form capable of being driving in a predetermined direction 118 toward the article 20 for applying a load.

Figure 6B:
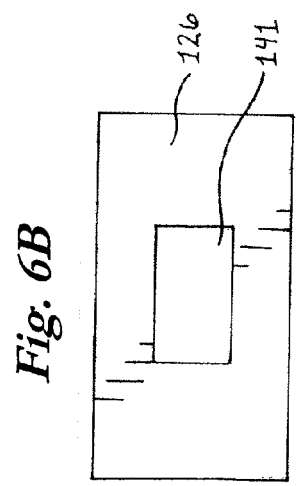
FIG. 6B is a perspective view of the horizontal support member of the load applying device of FIG. 6A with an opening therethrough to allow passage of the driven member.
Figure 6A:
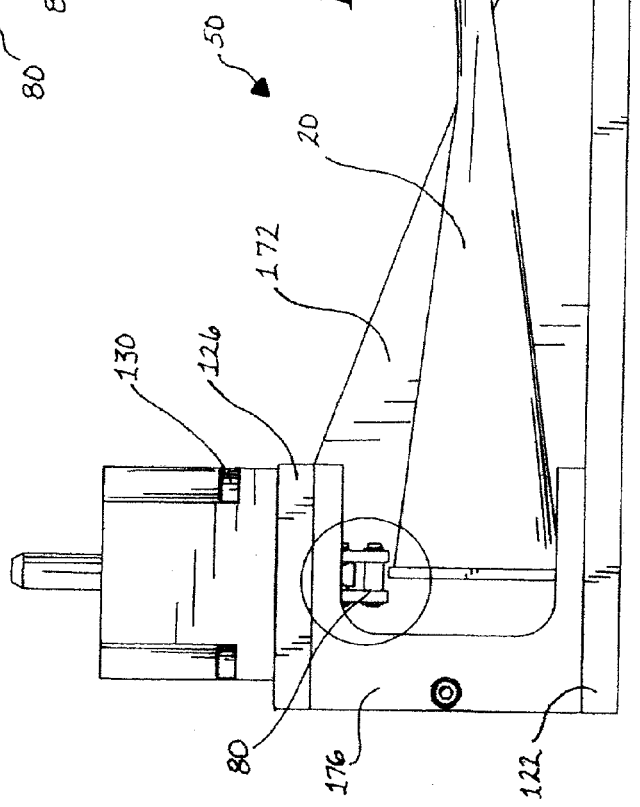
FIG. 6A is a side-elevational view of the load applying device showing a drive motor for advancing a drive screw so that a roller bearing member is driven against the blade.

Frame 122 of the x-ray diffraction apparatus 10 mounts the x-ray diffraction device 40 and the load applying device 50 including the drive assembly 120 thereof. In one embodiment, the drive assembly 120 may be fixedly mounted to the frame 122 as depicted in FIG. 6A. In FIG. 6A, the drive assembly 120 is mounted to a horizontal support member 126 that is elevated to extend over and parallel to base 128. For example, bolts 130 may be used to affix the drive assembly 120 to the horizontal member 126. In this embodiment, the horizontal support member is provided with a through hole 141, as depicted in FIG. 6B, positioned and sized to allow the driven member 114 to pass therethrough. In this form, a bearing mount or shackle assembly 131 is provided to pivotally mount the bearing member 80 to the end of the drive screw 114. Such an assembly 131 aids in keeping the bearing member 80 in engagement with the article 20 and maintaining contact therewith as the blade 20 is driven downwardly. By pivotally mounting the bearing member 80 to the drive screw 114 via the shackle assembly 131, the likelihood that the bearing member 80 will slide off of the blade 20 due to deflection of the blade while applying the load is reduced.

In an alternative embodiment as depicted in FIGS. 1-3 and 5, the drive assembly 120 is pivotably mounted to the frame 122 to allow the driven member 114 to pivot as load is applied to the held rotor blade 20. In this embodiment, the frame 122 is provided with a pair of upstanding spaced pivot supports 134 and 136 with the drive assembly 120 pivotally mounted therebetween. The drive assembly 120 includes a pivotal bracket mount 140 fixedly supporting the drive 84 thereunder. The pivot mount 140 has a U-shaped configuration with side arm portions that extend along the inner surface of upstanding pivot supports and which are pivotably connected thereto via a pair of pivot pins 144 passing through aligned through apertures in the supports 134, 136 and arms of the pivot mount 140. Further, in this embodiment, the horizontal support 126 (see FIG. 5B), which supports the pivot supports 134, 136, is provided with an opening 141 of a size sufficient to allow the pivotally mounted motor 84 to hang in alignment therewith, therein, or thereabove and to pivot unimpeded by the structure of the horizontal support 126.

Due to the configuration of the article 20 to be tested, placing a vertical downward load on the article may not cause the article 20 to deflect in a corresponding vertical downward direction in response to the vertical downward loading applied thereto. For example, the blade 20 as depicted in FIG. 1 has an approximate 90° twist or rotation of the broad portion 148 of the blade body 149 as it extends along the length of the blade body. Because of the twisted configuration of the blade body 149, an exclusively vertical downward directed force may cause the blade to deflect both downwardly and to one side. For example, when a downward force is applied to such an article at an end 150 opposite its fixed end 154, the blade body 149 will slightly to rotate about its axis 24 counter to the shaped twist in the blade and toward a generally flatter configuration thereof, thereby slightly reducing the 90° twist of the blade body 149. As illustrated, the free end 150 of the blade 20 has a transverse end flange 151 extending normal to the longitudinal axis 24 of the elongate blade body 149. The roller bearing 80 engages along the top side edge 152 of the end flange 151. As the blade body 149 deflects and twists as it is loaded, there is the risk that the roller bearing 80 could disengage from the end flange 151. By providing a pivot mount 140 for the drive assembly 120, constant contact of the bearing member with the blade 20, and more specifically with the end flange 151, is maintained. Further, by pivotably mounting the drive assembly 120, the bearing member will maintain a loading direction approximately normal to the end of the blade 150 to which the load is being applied as the blade 20 is being deflected and twisted. In this manner, the deflection distance of the blade end 150 will more closely correspond to the driven distance of the drive screw 114 in engagement with the blade end 150. The deflection and twisting of the blade 20 along with the corresponding pivoting of the driven member 114 of the drive assembly 120 is shown is ghost-lining and in an exaggerated form, for illustrative purposes, in FIG. 3.

As illustrated, the load applying mechanism 58 is spaced along the frame base member 128 from the mounting device or fixture 54 which holds the article 20 during application of loads thereto and x-ray diffraction testing thereof. For example, the mounting device 54 may be positioned to hold one end or end portion 154 of the article 20 to be tested. Preferably, the one end 154 held by the mounting device 54 is the end of the article 20 that is fixed to a driven portion when the article is in service. For example, when a rotor blade 20 is in service, the end of the blade 154 proximal to a driven rotor hub will have the highest concentration of stress relative to the rest of the blade. Hence, this end of the rotor blade 154 is used for being fixed to the mounting device 54 because the highest amounts of stress are focused at or near this end 154 and the loads applied during testing can be provided in a direction that emulates loads that are experienced by the blade while in service. The mounting device 54 preferably is configured to hold the one end 154 of the article 20 in a fixed relation to the mounting device 54 so as to extend in a cantilevered fashion therefrom to be in alignment under the load applying mechanism 58. Therefore, when the load applying mechanism 58 places a load on the article 20, a portion of the article is deflected. The mounting device 54 may be a clamp, bracket, provide a dovetail relationship with a shape of the end 154 of the article 20 or any other form that is capable of holding the end of the article 20 in a fixed relation to the mounting device 54 and in a cantilevered fashion extending therefrom. For example, the article 20 may be provided with a projection 155 and the mounting device 54 may be provided with a corresponding mating recess 156. As depicted in FIGS. 1-3, the projection 155 may be a complex dovetail or fir-tree configuration and the recess 156 has a corresponding mating configuration thereto so that the end projection is received tightly in the recess 156 to fix the blade end 154 relative to the mounting device 54.

As described above, the other end or end portion 150 of the article that is engaged by the bearing member 80 is deflected downwardly when a sufficient load is applied. This deflection in combination with the one end 154 of the article 20 being held in a fixed relation and in a cantilevered fashion creates stress at least in a general area of the article 20 adjacent the mounting device 54. Because of the increased stress created at this location, the x-ray emitter 62 may be directed at this increased stress area 158 in order to detect the greater changes in stress in the unloaded and loaded, or undeflected and deflected, states. By way of example and without limitation, a deflection distance of 10 mm at the end 150 of the blade 20 has been found to generate change in the measured total stress value compared to the measured residual stress value of the undeflected blade 20. Accordingly, with the bearing member 80 engaged with the undeflected blade 20 at the end flange 151 thereof, the driven screw 114 is preferably driven to be advanced 10 mm along its axis 119. While lesser or greater deflection distances may be applied, it has been found that this deflection distance does not damage the blade 20. Further, it has been determined that such a deflection distance will generate a strain value of approximately 2000 microstrain at the measured area 158. As the deflection distance and the generated strain are closely related, either value may be used in generating the slope values as described herein. Accordingly, the term load or loading as used herein for measurement and calculation purposes also encompasses the use of either deflection distance or strain for these purposes.

As depicted in FIG. 6A, the drive assembly 120 is fixed to the elevated support member 126 spaced above the base 128 in a plane parallel with the base 128. In FIGS. 1-3, the horizontal support member 126 instead has the upstanding pivot supports 134, 136 extending upward therefrom. In this case, as described above, the drive assembly has clearance with support member 126 to allow for pivoting with respect thereto. The horizontal support member 126 is provided with an opening therethrough (FIG. 6B) positioned and sized for the driven member 114 to pass therethrough for driving the article held beneath the horizontal support member 126 and applying a predetermined load thereto.

The horizontal support 126, as described above and depicted in FIG. 5B, is provided with a larger opening, of a size sufficient to allow the motor 84 of the drive assembly 120 to hang therein and configured to avoid interference with pivoting of the motor 84 so that it can pivot in an unimpeded fashion. The horizontal support member 126 is elevated from the base 128 by three walls; an end wall 168, a gusset wall 172, and a C-shaped wall 176. The C-shaped wall is provided such that the article 20 may be easily inserted and removed for testing. The base 128 may further support an elevating block 180 positioned to elevate the mounting device 54 to an appropriate height. Finally, the base 128 may be provided with one or more bolt holes 184 to allow the loading device 50 to be fixed in a housing for the x-ray diffraction apparatus 10.

The x-ray diffraction system 5 includes a controller or control system 200 for controlling operation of the x-ray diffraction device 40 and load applying mechanism 58 as schematically shown in FIG. 2. In one aspect, the controller 200 is operable via an interface or input 205 to cause the emitter 62 to direct x-rays at the held article 20 in an unloaded condition before the load applying mechanism 58 applies a load to the article 20, and is then further operable to cause the load applying mechanism 58 to apply a predetermined load to the article 20 and maintain the load while again causing the emitter 62 to direct x-rays at the article 20. Further, the controller 200 may be configured to automatically undertake any or all of the aspects and steps of testing and conducting analysis of an article to non-destructively determine the characteristics of the underlying material. For example, the system 5 may be configured such that after the article 20 is placed in the holding mechanism 54, the entire testing and analysis process may be automatically initiated by operating an actuator for the system 5, e.g. setting the actuator for the system 5 to "START."

In general, the x-ray diffraction system herein is capable of generating different loads on an article to be tested and using x-ray diffraction to non-destructively test a material characteristic of the overlying material 32 of an article 20. As previously described, the overlying material 32 covers the underlying material 22, thereby preventing analysis of the underlying material by x-ray diffraction techniques unless at least some of the overlying material 32 is removed.

The x-ray diffraction device 40 is provided for directing x-rays at the article 20 and detecting x-rays diffracted from the material. The x-rays diffracted from the material contain information relating to material characteristics of the overlying material, for example, the residual stress of the overlying material when the article is in an unloaded, or undeflected, state. A load applying device 50 is also provided for holding the article and generating different load conditions on the article 20. The controller 200 is electronically connected to the x-ray diffraction device for measuring a material characteristic of the overlying material of the article to be tested. The controller 200, may be hard-wired to perform its specific function or may otherwise, be wholly-programmable. In general, the controller 200, would be electrically connected to at least the x-ray diffraction device 40 and configured to control the emission of x-rays from the emitter 62 and receive information relating to the detection of x-rays diffracted from the article 20 via the one or more x-ray detectors 66, 68. For example, the x-ray detectors may be electronically connected to the controller 200 via data cables 208 attached to the detectors 66, 68. Additionally, the controller may be electrically connected to and configured to control the load applying device 50 and to cause the drive 84 to apply different loads to deflect to the article 20 as has been described. By generating different loading conditions on the article and measuring the material characteristic under the different loading conditions, two different material characteristic values are generated.

The controller 200 has various functional units that are configured to carry out specific functionalities desired for the x-ray diffraction testing system 5 herein. These units may include, a processing unit 210, a memory unit 220, which can have database 230 stored therein, and a comparison unit 240. These units are electrically connected to allow them to cooperate and share information to perform the analysis described herein.

The processing unit 210 is configured to process the information relating to the material characteristics determined under the different loads and the values of the different loads and to calculate a slope of the material characteristics of the overlying material versus the load conditions. As is known, a slope may be calculated generally using the formula $m=(y_2-y_1)/(x_2-x_1)$, where m=slope, the $x_1$ and $x_2$=measured load values, and $y_1$ and $y_2$=measured stress values. Further, as discussed above, the load values may instead be corresponding deflection distances or strain amounts. The processing unit may further be provided with software that is programmed for determining the residual or total stress of the article 20 based on the data collected from the one or more x-ray detectors 66, 68 and the different loads applied to the article by the drive 84.

As described above, it has been determined that material characteristics of overlying material 32 of articles is directly responsive to material characteristics of the underlying material 22 in an article. Specifically, it has been determined that a comparison of stress measurements of a polycrystalline layer 32 under different loads can be related to the elasticity of the underlying crystalline material 22. Further the elasticity of the underlying crystalline material 22 varies dependent on the grain orientation. Therefore, it has been determined that by generating a slope value based on the stress measurements under different loads for a plurality of articles by using the system. The articles may then be destructively tested to determine the orientation angle of the crystalline material. This information is then correlated, providing a body of information for that configuration of the article that can then be used to infer underlying orientation angles of similar articles based on determining the slopes alone.

For example, as depicted in FIG. 9, a representative graph is provided plotting stress measurements at zero deflection and with the blade loaded to have a predetermined deflection distance for three blades and showing the slopes of residual stress versus deflection for each blade. As described above, the x-ray diffraction measurement of the stress when the blade is unloaded, or in an undeflected state, will provide a residual stress value. When a load is applied to the blade, e.g when the blade is deflected, the x-ray diffraction measurement will be of a total stress value which is the combination of the inherent residual stress of the blade plus the applied stress. As is known in the art, stress values are often reported in megapascal (MPa) or thousands of pounds per square inch (ksi). Accordingly, the term stress herein encompasses both residual stress at zero loading or total stress at a loading value on the blade or a deflection distance of the blade greater than zero.

For each of the blades, two stress values are measured in the polycrystalline layer 22 under two different deflections. For the purposes of the example, the deflection distances are zero and 10 mm. Therefore, the values that are plotted at zero load on the x-axis of the plot are residual stress values and the values plotted at the 10 mm load on the x-axis are total stress values. The slopes of each of the samples are plotted on the graph. Samples A and B further underwent destructive testing to determine the grain orientation angle of the underlying crystalline material. Sample A is determined to have a grain orientation of 0° (in line with the longitudinal axis of the blade) and Sample B is determined to have a grain orientation of +20° from the axis of the blade. The Sample C was not destructively tested. By comparing the slopes of the three samples, it can be seen that Samples A and C have a similar slope, while Sample B has a different slope. Therefore, it would be determined that Samples A and C would have the same orientation angle. It will also be noted in the representative graph that the residual stress values at zero deflection distance are not the same for samples A and C as different articles may have different total stress values under similar loads. However, it is not the particular residual stress and total stress readings that are important, but rather the response of the overlying layer to the elasticity of the underlying material.

The memory unit 220 is adapted to contain a database 230 of slopes correlated to material characteristics of similarly configured articles 20 having known orientation angles. The slope that is calculated by the processing unit 210 is then compared by a comparison unit 240 of the controller 200 to slopes contained in the database 230 to determine the material characteristic of the underlying material 22. By comparing the calculated slope of the article being tested 20 to the slopes of similar articles having known orientation angles, the orientation angle of the tested article 20 can be inferred. Hence, the article is tested in a non-destructive fashion, and the characteristic of the underlying material 22 can then be used determine whether or not to place the tested article into service. Predetermined variance allowances may be determined by the manufacturer or user to indicate what an acceptable deviation from the preferred angle would be considered allowable for articles 20 to be paced into service. For example, limits may be set to indicate that articles 20 having crystal orientation angles of greater than ±15° from the preferred angle should be rejected.

The comparison unit 240 may further be provided with software configured to determine the material characteristic of the underlying material in the article. In one embodiment, the software identifies the slope in the database 230 closest to the slope value of the tested article 20 and assigns the article 20 the material characteristic of the underlying material correlated to the closest slope. Alternatively, the software identifies a plurality of slope values in the database 230 close to the slope value of the tested article and determines an orientation angle based on the plurality of slope values such as based on the average or mean value of the slopes.

The x-ray diffraction system 5 may further be provided with an interface or input 205 for the controller 200 to allow an operator to load data to the memory unit and to control operation of the x-ray diffraction device and load applying device as previously discussed. As described above, the system may be used to determine slopes of similarly configured articles by measuring a material characteristic, e.g. residual stress and total stress, on the surface of an article. When creating the database 230, the similarly configured articles would then be destructively treated, e.g. by forming a coupon from the blade, for testing such as by x-ray diffraction or other techniques, to determine a desired material characteristic, e.g. the orientation angles. The determined orientation angles could then be entered into the controller 200 via the input 205. In addition, the processing unit 210 may further be provided with software to correlate the slope of the similarly configured articles and the input material characteristic, or orientation angle. This correlated information would then be stored in the database 230 for subsequent comparison to tested articles 20.

Figure 10:
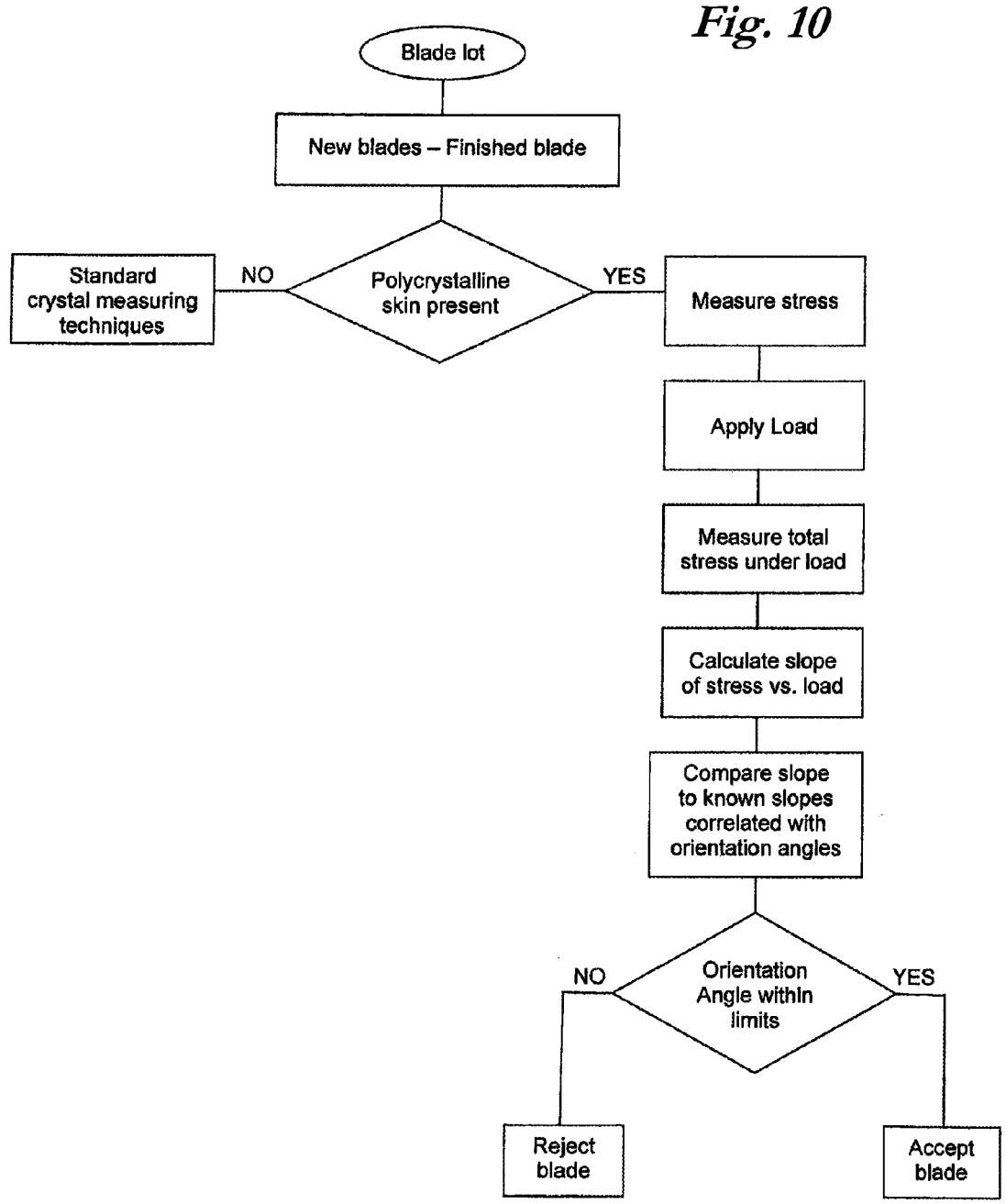
FIG. 10 is a flow diagram showing the steps for non-destructively determining the orientation angle of the underlying crystalline material of a rotor blade having an outer polycrystalline skin.

The methods of the present invention non-destructively determine grain orientation of a crystalline material in an article where the crystalline material is underlying to an overlying polycrystalline layer. Such method may be used for determining which articles, for example rotor blades, should be placed into or kept in service based on the determination of the article's underlying crystalline orientation angle. A general depiction of a process in accordance with the invention is provided in the flowchart of FIG. 10.

In a one aspect of the method, a first residual stress measurement is obtained for the overlying polycrystalline layer of a blade under a first predetermined loading condition. The first predetermined loading condition may be of any value. Preferably, the first predetermined loading condition is the blade with zero load applied so that the blade is in an undeflected state. The stress may be measured by any stress measurement technique known in the art including x-ray diffraction techniques. For example, the preferred measurement technique of d v. $Sine^2_\psi$ may be used in measuring the stress. Additionally, single exposure, double exposure, or similar techniques may used to determine stress After a first stress measurement, a load is applied that is different from the load applied when measuring the first stress value. In one embodiment, the load value generates a predetermined deflection distance in the end 150 of the blade 20, which can also be correlated to a strain value. While the different load is applied, a second stress measurement is obtained. The stress values and the different load values are used to calculate a slope value for the article. As described above, the polycrystalline layer is directly responsive to the underlying crystalline material. Because of this, if the grain orientation of the underlying crystalline material varies in a group of tested samples, this will be reflected in the elasticity of the article and in turn on the change in stress values between the different loading conditions. Therefore, the slope of the tested article can be compared to samples that have known stress versus load slopes and known orientation angles to determine the orientation angle of the tested article.

Preferably, when testing the article for the first and second stress measurements under the different loading conditions, the residual stress measurements are taken at the same location in the article. This provides a better data set by which to compare the change in the residual stress measurement under the different loads and the calculated slope. Furthermore, preferably when determining the slope of the similarly configured articles used in generating the database 230, the same loads are used and the stress is measured at the same location for each of the similarly configured articles as will be used and measured on the subsequent tested articles.

Figure 11:
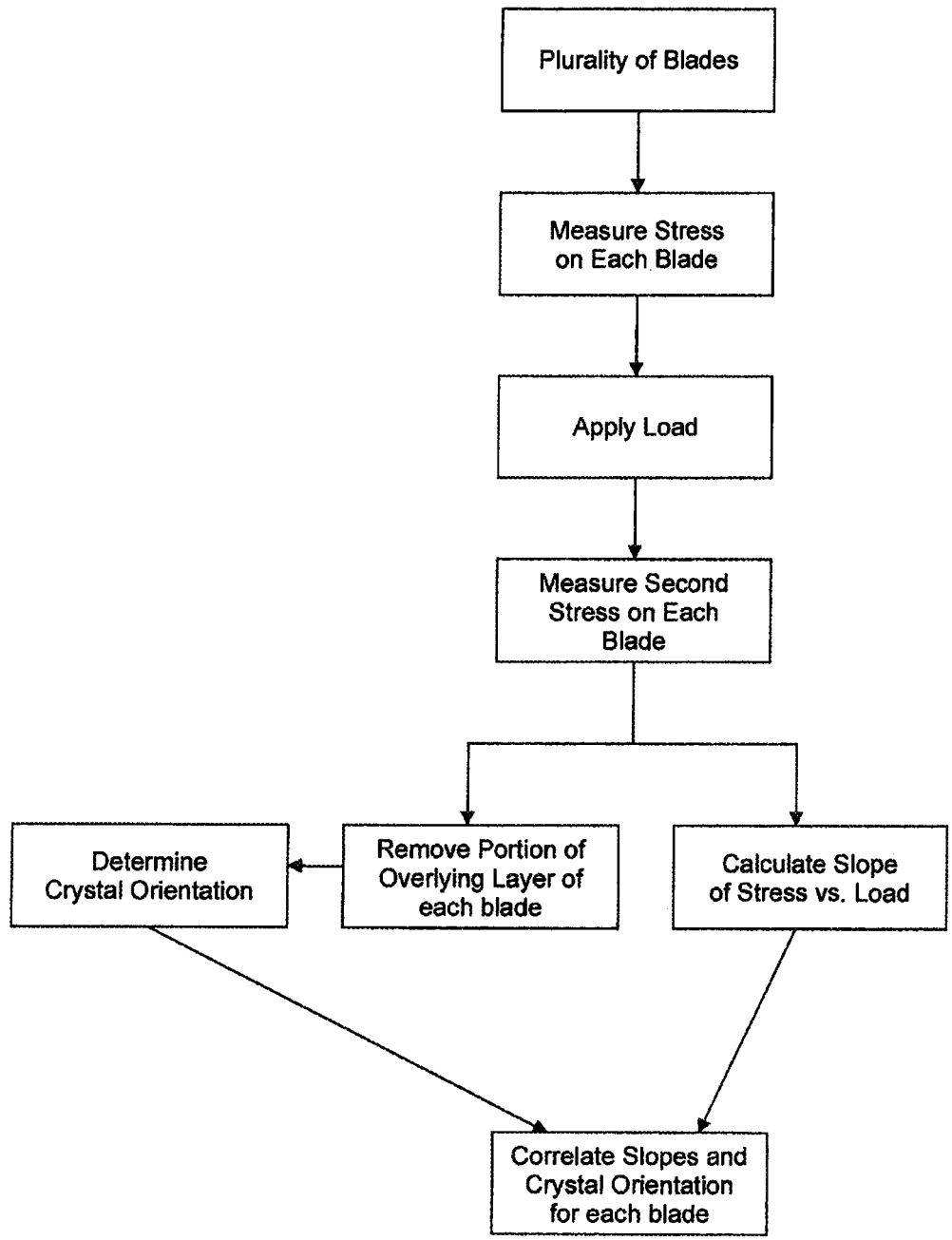
FIG. 11 is a flow diagram showing the steps for generating correlated data of slopes of stress versus load for overlying polycrystalline material of rotor blades and known orientation angles of the underlying crystalline material of the blades.

For each of the similarly configured articles, the underlying crystalline material is directly measured to determine the orientation angle. Due to the overlying polycrystalline layer, at least a portion of the polycrystalline layer is removed to expose a portion of the underlying crystalline material. The removal of the portion of the polycrystalline layer, for the purpose of this application, is considered destructive to each of the similarly configured articles. The underlying crystalline material is then measured to determine the orientation angle of the crystal. Tests for directly determining an exposed crystal are known in the art. These may include, but are not limited to, LAUE analysis, pole figure analysis, electron microscopy, and metallurgical techniques. The crystal orientation is then correlated to the slopes generated for each of the similarly configured articles. The general process for generating this information and correlating the slopes and orientation angles is depicted in the flowchart of FIG. 11.

The developed correlated information may be used to generate a database of information that is then used to nondestructively determine the orientation angle of articles to be tested. Once the database has been established, each subsequently tested article may be measured to determine stress values under the same loading conditions as used to generate the slopes in the database of the similar articles. The measured values may then be used to generate a slope which is then compared to the slopes in the database. In comparing the slope to the database of slopes, similar slopes of the similarly configured articles are identified. The orientation angles correlated to these slopes are then assigned to the tested article. For example, the orientation angle of the closest slope value may be assigned to the tested article or the average of angles correlated to a set of slopes comparable to the tested slope may be assigned to the article. By using the methods described herein the orientation angle of the underlying crystalline material for a tested article may be determined without direct measurement of the underlying material. Also, by using the methods described herein the orientation angle of the underlying crystalline material may be determined in a manner non-destructive to the article being tested. In practice, it has been determined that the systems and processes as described herein can accurately detect blades 20 that have an orientation angle outside an acceptable range in blades 20 formed from SX and DS materials having an overlying skin. This has further been confirmed by subsequently destructively measuring these blades to confirm the determined angle.

While there have been illustrated and described particular embodiments and methods of the present invention, it will be appreciated that numerous changes and modifications will occur to those skilled in the art, and it is intended tin the appended claims to cover all those changes and modifications which fall within the true sprit and scope of the present invention.

What is claimed is:

1. An x-ray diffraction apparatus comprising:
   a mounting device configured to hold an article to be tested;
   an x-ray emitter for directing x-rays at the held article;
   a load applying mechanism for exerting a predetermined load on the article;
   an x-ray detector for detecting diffracted x-rays from the held article under different load conditions; and
   a control system for controlling operation of the x-ray emitter and the load applying mechanism, and wherein the control system causes the x-ray emitter to direct x-rays at the held article in an unloaded condition before the load applying mechanism applies a load, and causes the x-ray emitter to direct x-rays at the held article in a loaded condition where the load applying mechanism applies the predetermined load to the held article.

2. The x-ray diffraction apparatus of claim 1, wherein the load applying mechanism includes a rolling bearing member for being engaged against the article, and a drive for driving the rolling bearing member into engagement with the article.

3. The x-ray diffraction apparatus of claim 1, wherein the load applying mechanism has a drive assembly including a driven member that is shifted in a predetermined direction toward the article for applying the predetermined load thereto, and
   a frame to which the drive assembly is pivotably mounted to allow the drive member to pivot as the driven member is shifted in the predetermined direction.

4. The x-ray diffraction apparatus of claim 1, wherein the mounting device and the load applying mechanism are spaced from each other with the mounting device configured to hold the article in a fixed relation thereto and in a cantilevered fashion extending therefrom to be in alignment under the load applying mechanism so that application of the predetermined load to the fixed article by the spaced load applying mechanism causes deflection of the article.

5. The x-ray diffraction apparatus of claim 1, wherein the x-ray emitter is arranged to direct x-rays to a location adjacent to the mounting device and the held article thereat.

6. An x-ray diffraction system for generating differential loading on an article to be tested using x-ray diffraction to non-destructively determine a material characteristic of an underlying material of the article under an overlying material, the underlying material otherwise not subject to non-destructive x-ray analysis, the x-ray diffraction system comprising:
   an x-ray diffraction device for directing x-rays at the article and detecting x-rays diffracted from the overlying material of the article;
   a load applying device for holding the article and generating different load conditions on the article;
   a controller connected to the x-ray diffraction device for measuring a material characteristic of the overlying material of the article to be tested under the different load conditions;
   a processing unit of the controller for calculating a slope of the material characteristic of the overlying material versus load conditions for the article to be tested;
   a memory unit of the controller including a database containing a plurality of slopes correlated to material characteristics of underlying material of a plurality of similarly configured articles; and
   a comparison unit of the controller for comparing the slopes in the database of the memory unit to the calculated slope from the processing unit and determining the material characteristic of the underlying material of the article to be tested without subjecting the underlying material thereof to non-destructive material testing techniques.

7. The x-ray diffraction system of claim 6, wherein the comparison unit includes software configured to determine the material characteristic of the underlying material in the article to be tested by indentifying the slope of the database closest to the calculated slope and assigning to the article the material characteristic of the underlying material correlated to the identified slope.

8. The x-ray diffraction system of claim 6, wherein the x-ray diffraction device comprises an x-ray emitter and at least one x-ray detector.

9. The x-ray diffraction system of claim 8, wherein the controller is further connected to the load applying device, and wherein the controller causes the x-ray emitter to direct x-rays at the held article in an unloaded condition before the load applying device applies a predetermined load to the held article.

10. The x-ray diffraction system of claim 6, wherein the plurality of slopes of the plurality of similarly configured articles in the database are calculated slopes of material characteristics of overlying material of the plurality of similarly configured articles versus the load conditions.

11. The x-ray diffraction system of claim 10, further comprising an input of the controller for input of material characteristics of the underlying material of the plurality of similarly configured articles determined outside the system using destructive analysis, wherein the processing unit includes software to correlate the slopes of the similarly configured articles to the input material characteristics.

12. A method comprising:
   providing an article to be tested including different materials with one of the materials being responsive to the other material under predetermined test conditions;
   measuring a predetermined material characteristic of the one material for a plurality of similarly configured articles to the article to be tested under the predetermined test conditions;
   measuring a different material characteristic of the other material for the plurality of similarly configured articles;
   correlating the measured predetermined material characteristic to the measured different material characteristic for each one of the similarly configured articles;
   testing the article to be tested by measuring the predetermined material characteristic of the one material for the article under the predetermined test conditions;
   comparing the measured predetermined material characteristic of the one material for the article to be tested to measured predetermined material characteristics of the one material for the similarly configured articles; and
   determining the different material characteristic for the other material of the article to be tested based on the comparison of the measured predetermined material characteristic for the article to be tested with the similarly configured article without requiring measurement of the different material characteristic of the other material of the article to be tested.

13. The method of claim 12, wherein the measuring of the predetermined material characteristic of the one material for a plurality of similarly configured articles under the predetermined test conditions includes:
   measuring a first stress at a location in the one material under a first loading condition;
   applying a second loading condition different than the first loading condition;
   measuring a second stress at the same location in the one material under the second loading condition; and
   calculating a slope of the stress versus the predetermined loading conditions to provide the predetermined material characteristic.

14. The method of claim 13, wherein the measuring of the first stress and second stress is performed using x-ray diffraction techniques.

15. The method of claim 12, wherein the measuring of the different material characteristic of the other material for the plurality of similarly configured articles includes;
   removing at least some of the one material from each of the similarly configured articles to provide access to the other material; and
   analyzing the accessible other material to determine the different material characteristic.

16. The method of claim 12, wherein the method further comprises developing a database of the correlated predetermined material characteristics and measured different material characteristic for each one of the similarly configured articles.

17. The method of claim 16, wherein comparing measured predetermined material characteristic of the one material for the article to be tested to measured predetermined material characteristics of the one material for the similarly configured articles includes, referencing the database to identify similarly configured articles having predetermined material characteristics similar to the predetermined material characteristic of the article to be tested.

18. The method of claim 17, wherein the different material characteristic for the other material of the article to be tested is determined by referencing the database to identify the different material characteristics of the identified similarly configured articles having predetermined material characteristics similar to the predetermined material characteristic of the article to be tested and assigning the different material characteristic to the article to be tested.

19. The method of claim 12, wherein the measuring of the different material characteristic is performed using techniques selected from the group consisting of LAUE analysis, pole figure analysis, electron microscopy, sonic analysis, ultrasonic analysis, eddy current techniques, electromechanical techniques, electromagnetic techniques and metallurgical techniques.

20. The method of claim 12, wherein determining of the different material characteristic of the article to be tested is non-destructive.

21. A method for determining an unknown orientation angle of an underlying crystalline material in an article to be tested having an overlying polycrystalline layer, the method comprising:
(1) measuring a first stress at a location in the polycrystalline layer to provide a first stress value;
(2) applying a predetermined load to the article greater than that to which the article is exposed to during the measurement of the first stress;
(3) measuring a second stress under the predetermined load at the same location in the polycrystalline layer to provide a second stress value;
(4) calculating a slope of stress versus load; and,
(5) comparing the slope to previously determined slopes of similarly configured articles having underlying crystalline material of known orientation angles and overlying polycrystalline material to determine the unknown orientation angle.

22. The method of claim 21, wherein the previously determined slopes of articles having various known orientation angles are provided by the steps comprising:
(a) providing a plurality of similarly configured articles having underlying crystalline material and overlying polycrystalline material to the article to be tested;
(b) measuring the first stress at the location in the polycrystalline layer of the plurality of similarly configured articles to provide first stress values;
(c) applying the predetermined load to each of the similarly configured articles;
(d) measuring the second stress under the predetermined load at the same location in the polycrystalline layer on the plurality of similarly configured articles to provide second stress values;
(e) calculating slopes of stress versus load for each of the plurality of similarly configured articles to provide the previously determined slopes;
(f) measuring the orientation angle of the underlying crystalline material for each of the plurality of similarly configured articles; and
(g) correlating the predetermined slopes and orientation angles for each for the plurality of the similarly configured articles to provide the various previously determined slopes of articles having known orientation angles.

23. The method of claim 21, wherein the step of measuring of the first stress comprises: directing x-rays at the location in the polycrystalline layer, detecting the x-rays diffracted from the location, and calculating the first stress from the detected x-ray diffraction.

24. The method of claim 23, wherein the calculating of the first stress is performed using a d v. $\text{Sin}^2\psi$ technique.

25. The method of claim 21, wherein during the step of measuring of the first stress, no load is applied to the article.

26. The method of claim 25, wherein when no load is applied to the article, the article is in an undeflected state.

27. The method of claim 21, wherein the step of applying the predetermined load to the article comprises deflecting the article a predetermined distance.

28. The method of claim 21, wherein the step of applying the predetermined load to the article comprises deflecting the article to generate a predetermined strain value.

29. The method of claim 21, wherein the step of measuring of the second stress comprises: directing x-rays at the location in the polycrystalline layer of the article under the predetermined load, detecting the x-rays diffracted from the location, and calculating the second stress from the detected x-ray diffraction.

30. The method of claim 29, wherein the calculating of the second stress is performed using a d v. $\text{Sin}^2\psi$ technique.

31. The method of claim 21, wherein the unknown orientation angle of the underlying crystalline material is determined without direct measurement of the underlying material.

32. The method of claim 21, wherein determining the unknown orientation angle is non-destructive to the article to be tested.

* * * * *